(12) United States Patent
Inoue et al.

(10) Patent No.: US 7,829,335 B2
(45) Date of Patent: Nov. 9, 2010

(54) METHOD OF DIFFERENTIATION INDUCTION TO OSTEOBLASTS

(75) Inventors: Akira Inoue, Yokohama (JP); Hitoshi Hatayama, Yokohama (JP); Hiroshi Suganuma, Tokyo (JP); Kunio Awazu, Nishinomiya (JP); Toshihiro Kushibiki, Ibaraki (JP)

(73) Assignee: Sumitomo Electric Industries, Ltd., Osaka (JP)

( * ) Notice: Subject to any disclaimer, the term of this patent is extended or adjusted under 35 U.S.C. 154(b) by 126 days.

(21) Appl. No.: 11/892,061

(22) Filed: Aug. 20, 2007

(65) Prior Publication Data

US 2008/0057580 A1    Mar. 6, 2008

(30) Foreign Application Priority Data

Aug. 23, 2006  (JP) ............................. 2006-226212
Feb. 13, 2007  (JP) ............................. 2007-031630

(51) Int. Cl.
    *C12N 5/00*    (2006.01)
(52) U.S. Cl. ...................................... 435/377; 435/375
(58) Field of Classification Search .............. 435/377, 435/375
    See application file for complete search history.

(56) References Cited

FOREIGN PATENT DOCUMENTS

| JP | 2004-129549 | 4/2004 |
| JP | 2005-124460 | 5/2005 |
| JP | 2005-247740 | 9/2005 |

OTHER PUBLICATIONS

Abromavitch-Gottlib et al. "Low level laser irradiation stimulates osteogenic phenotype of mesenchymal stem cells seeded on three-dimensional biomatrix," *Lasers in Medical Science*, vol. 20, pp. 138-146, 2005.
Dörtbudak et al. "Biostimulation of bone marrow cells with a diode soft laser," *Clinical Oral Implants Research*, vol. 11, pp. 540-545, 2000.
Yamamoto et al. "Stimulation of MCM3 Gene Expression in Osteoblast by Low Level Laser Irradiation," *Lasers in Medical Science*, vol. 16, pp. 213-217, 2001.
Stein et al. "Low-Level Irradiation Promotes Proliferation and Differentiation of Human Osteobalsts in Vitro," *Photomedicine and Laser Surgery*, vol. 23, No. 2, pp. 161-166, 2005.
Fu et al. "The circadian modulation of leptin-controlled bone formation," *Progress in Brain Research*, vol. 153, pp. 177-188, 2006.
Kushibiki et al. "A blue-violet laser irradiation stimulates bone nodule formation of mesenchymal stromal cells by the control of the circadian clock protein," *Proc. of SPIE*, vol. 6435, pp. 64351B-1-64351B-5, 2007.
Balsalobre, et al. *Science* 289:2344-2347, 2000.
Ozawa, et al. *Bone* 22(4):347-354, 1998.
English language Abstract of JP 2005-124460.
English language Abstract of JP 2004-129549.
English language Abstract of JP 2005-247740.
Jaiswal et al., "Osteogenic Differentiation of Purified, Culture-Expanded Human Mesenchymal Stem Cells In Vitro" *Journal of Cellular Biochemistry* 64:295-312 (1997).

*Primary Examiner*—Anne-Marie Falk
*Assistant Examiner*—Magdalene K Sgagias
(74) *Attorney, Agent, or Firm*—Greenblum & Bernstein, P.L.C.

(57) ABSTRACT

The invention offers a technique that selectively differentiation-induces mesenchymal stem cells, which can differentiate to cells that constitute various tissues and organs, to osteoblasts. In addition, the invention offers a technique that differentiation-induces mesenchymal stem cells to osteoblasts with a simple operation that needs only short time and that is noninvasive. The inventors have found that the switch for the differentiation induction to osteoblasts is turned on by translocating biological clock-relevant factors existing in mesenchymal stem cells from the cells' cytoplasm to the cells' nucleus. The inventors have also found that the switch can be turned on by irradiating the cells for a short time with a lightwave having a specific wavelength that is noninvasive.

8 Claims, 4 Drawing Sheets

Bar: 20 μm

SEQUENCE LISTING

<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic mouse cryptochrome siRNA
<220> FEATURE:
<223> OTHER INFORMATION: Description of Artificial Sequence: Synthetic
      mouse cryptochrome siRNA

<400> SEQUENCE: 1
gcagacugaa uauugaaagt t                                              21

<210> SEQ ID NO 2
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic mouse cryptochrome siRNA
<220> FEATURE:
<223> OTHER INFORMATION: Description of Artificial Sequence: Synthetic
      mouse cryptochrome siRNA

<400> SEQUENCE: 2
ggcacuuaca cguuuggaat t                                              21

METHOD OF DIFFERENTIATION INDUCTION TO OSTEOBLASTS

BACKGROUND OF THE INVENTION

1. Field of the Invention

The present invention relates to a regeneration medicine, more specifically a method of differentiation-inducing mesenchymal stem cells to osteoblasts.

2. Description of the Background Art

The regeneration medicine is a medicine aiming not only to regenerate cells, a tissue, and an organ of a living body lost by an accident or illness but also to recover the function of them. The medicine is one of the great challenges in the clinical medicine in the 21st century.

For example, after an external injury or a bone neoplasm is removed surgically, so far the bone tissue has been treated for the recovery by taking out an autologous bone, such as a thigh bone of the patient himself or herself, to transplant it to the affected portion. However, this method requires a surgical treatment for a sound thigh bone in addition to the treatment of the affected portion, giving the patient a doubled burden. Furthermore, the medical expense is increased.

On the other hand, the regeneration medicine, which has been attracting attention recently, is a medical technique that focuses attention on stem cells capable of differentiating to practically all tissues and organs in a living body. More specifically, by giving a specific instruction to stem cells from the outside, the stem cells are differentiation-induced to cells that construct a targeted tissue or organ. Thus, the medical technique finally regenerates the lost tissue or organ.

It is known that such stem cells exist in various types. They exist in nearly all organs and tissues in a living body. In particular, among various types of stem cells, such as haematopoietic stem cells and neural stem cells, cells known as embryonic stem (ES) cells can differentiate to any types of tissue and have high proliferating ability. Therefore, the EC cells are expected to be applied, as universal cells, to the treatment of various diseases such as Parkinson's disease, myocardial infarction, spinal damage, leukemia, diabetes, and liver disease.

However, the EC cells are cells produced from an early embryo (a fertilized egg) after an elapse of five to seven days or so from the time of fertilization in human and after an elapse of three to four days or so in mouse. Consequently, there is a problem of ethics. Therefore, there are many hurdles to cross before the cells are put into practical use in the regeneration medicine.

In place of the EC cells, another type of stem cells has been attracting attention recently, which is mesenchymal stem cells existing in the bone marrow. The mesenchymal stem cells have a potential to have an ability close to that of the EC cells. It has been confirmed that the mesenchymal stem cells turn into the cells of the bone, cartilage, fat, heart, nerve, liver, and so on. As a result, the mesenchymal stem cells attract attention as the second universal cells.

If the mesenchymal stem cells can be used, they can be differentiation-induced into the bone cells at the outside of a living body to treat a patient by transplanting the bone cells to the affected portion. Therefore, in the field of the regeneration medicine, the researchers have been studying by paying attention to how to take out mesenchymal stem cells with a reduced burden on the patient and how to proliferate the taken-out stem cells to such an extent that they can be transplanted.

For example, Patent literature 1 has disclosed that there exists cells, which differentiate to osteoblasts, in the amniotic epithelial cell layer of the human and that by separating the amnion from the placenta to culture the cells at the outside of the living body, the differentiation induction to osteoblasts can be achieved.

In addition, another Patent literature 2 has disclosed a method of separating fibroblasts in which, first, extracellular matrixes existing in a piece of fat in the human are digested by a collagenase treatment to obtain a group of cells, second, a group of mature adipocytes is separated by centrifugation, and, third, the performing of the primary culture differentiation-induces them to osteoblasts.

In addition to the above-described studies on the separation and culture of cells, researchers have been studying on the analysis of the differentiation mechanism of the mesenchymal stem cells. For example, Patent literature 3 has reported that the manifestation of a brain and muscle arnt-like protein 1 (BMAL1) gene, which is one of the biological clock-relevant factors, is recognized in the process of the differentiation to mast cells.

Patent literature 1: the published Japanese patent application Tokukai 2005-124460.

Patent literature 2: the published Japanese patent application Tokukai 2004-129549.

Patent literature 3: the published Japanese patent application Tokukai 2005-247740.

However, the above-described Patent literature 1 has not stated that the cells that are supposed to be able to be differentiated to osteoblasts are mesenchymal stem cells. Instead, the literature has described that the cells are cells obtained by taking out from the amnion of the human. The literature has disclosed that because the human's amnion is a tissue derived from a fetal, the amnion can be easily taken out in a state that it is attached to the placenta of the mother's body. In addition, the literature has reported that because the fetal-derived amnion is used, the immune tolerance is manifested, so that even when it is transplanted to a different person, it has little tendency to cause rejection (see the paragraph [0013] in Patent literature 1). However, Class I of HLA is manifested. Therefore, it cannot be said that 100% immune tolerance is assured and consequently there is a risk that an unexpected rejection is caused after they are transplanted to the patient. Furthermore, the cells obtained from the amnion include cells that cannot be differentiation-induced to osteoblasts.

In addition, in the technique disclosed in Patent literature 2, the piece of fat can be taken out from the fat tissue of the patient himself or herself. Consequently, the rejection that Patent literature 1 may cause as a problem can be prevented. Nevertheless, as with Patent literature 1, Patent literature 2 has created a problem that cells that differentiate to osteoblasts cannot be separated with sufficient purity.

A problem common to Patent literatures 1 and 2 is that cells that differentiate to osteoblasts have not been able to be separated with sufficient purity. Consequently, even when the differentiation induction to osteoblasts has been successfully carried out at the outside of a living body, cells other than osteoblasts are also transplanted to the patient. Therefore, it is unclear whether or not the tissue or organ can be regenerated without problem as the one having a satisfactory function.

Furthermore, another problem common to Patent literatures 1 and 2 is that the separated cells require a few weeks for the preculture. In addition, to differentiation-induce the precultured cells to osteoblasts, the cells must be cultured at the outside of a living body for at least a few weeks by adding to the medium a specific differentiation-inducing factor, such as ascorbate, dexamethasone, and β-glycerol phosphoric acid.

In other words, the patient whose bone has been removed due to an external injury cannot be treated by the transplanting to the affected portion for at least one month. This is a considerably hard thing for the patient.

In both of Patent literatures 1 and 2, the switch for the differentiation induction is only the changing of the composition of the medium. If this approach is utilized in the future to a method in which only mesenchymal stem cells are transplanted into a living body to differentiate them later to osteoblasts, it will become necessary to administer a differentiation-inducing factor, such as ascorbate, dexamethasone, and β-glycerol phosphoric acid, to the affected portion that has been treated by the transplantation. Consequently, there exists a risk that the patient suffers an unexpected adverse reaction. Furthermore, as described above, mesenchymal stem cells have an ability to differentiate to the cells of the bone, cartilage, fat, heart, nerve, and liver. As a result, there is another risk that the foregoing differentiation-inducing factor exercises another function in the living body and differentiates to cells having another function at the affected portion.

In addition, Patent literature 3 has disclosed that the BMAL1 manifests itself in the process of differentiation to fat cells. However, the manifestation of the BMAL1 is controlled by using a technique in which a gene is introduced into the cells. Nevertheless, the technique for the control merely analyzes the mechanism of the manifestation of the BMAL1 at the molecular level. In other words, no novel findings have been disclosed on what type of instruction is to be given to mesenchymal stem cells in order to differentiate them to fat cells. The differentiation induction to fat cells are only performed by adding to the medium a differentiation-inducing factor, such as dexamethasone and isobutyl methylxanthine.

SUMMARY OF THE INVENTION

The present invention is made in view of the above-described problems. An object of the present invention is to offer a technique that selectively differentiation-induces mesenchymal stem cells, which can differentiate to cells constituting various tissues and organs, to osteoblasts.

Another object of the present invention is to offer a technique that differentiation-induces mesenchymal stem cells to osteoblasts with a simple operation that needs only short time and that is noninvasive.

To attain the foregoing object, the present inventors have studied intensively and have found that the switch for the differentiation induction to osteoblasts is turned on by translocating a biological clock-relevant factor existing in the cytoplasm of mesenchymal stem cells from the cytoplasm to the nucleus.

In addition, the present inventors have also found that the switch for the differentiation induction to osteoblasts can be turned on by irradiating cells with a lightwave having a specific wavelength that is noninvasive, rather than by the conventional method in which the switch for the differentiation induction to osteoblasts is turned on by adding a specific differentiation-inducing factor to the culture medium.

In other words, the present invention offers a method of differentiation-inducing cells, the method differentiation-inducing mesenchymal stem cells to osteoblasts by translocating biological clock-relevant factors of the mesenchymal stem cells from the cells' cytoplasm to the cells' nucleus.

In the above description, the term "biological clock-relevant factors" is used to mean factors relevant to a biological clock or body clock, and the term "factors" has a meaning including "protein," "DNA," and "RNA." In addition, the terms "circadian rhythm" and "diurnal cycle" are also used as terms having the same meaning as a biological clock. It is known that the types of molecule needed for the body clock in a living body to beat out the rhythm include, beside the foregoing BMAL1, a CLOCK, PERIOD (PER), and CRYPTOCHROME (CRY). These molecules beat out the rhythm of a biological clock singly or by forming a composite. It is known that the BMAL1 and CLOCK are positive-feedback agents in the adjustment of the clock, and the PERIOD and CRYPTOCHROME are negative-feedback agents.

In other words, although cryptochrome is a protein identified as a receptor of blue light, it is one of the molecules that adjust the biological clock in an animal cell. It is understood that the cryptochrome forms a composite with a PERIOD, is translocated from the inside of the cytoplasm to the inside of the nucleus, and inhibits the function of a transcriptional activator the CLOCK and BMAL have. Because the cryptochrome is a receptor of blue light in a plant, the cryptochrome may carry out the signal transduction using blue light in an animal cell, also. A mouse has already been produced in which the cryptochrome gene is knocked out, and it has been reported that when no cryptochrome exists, the rhythm becomes abnormal (see "Cell," Vol. 98, pp. 193-205, 1999).

The present invention also offers a method of differentiation-inducing cells, in which the biological clock-relevant factors can be translocated from the cytoplasm to the nucleus by irradiating the mesenchymal stem cells being cultured in a culturing container with a lightwave having a specific wavelength, which is a noninvasive means to the mesenchymal stem cells.

In addition, according to the present invention, the lightwave having a specific wavelength has no particular limitations on condition that the lightwave has a wavelength of 350 to 500 nm. As an example, however, a laser lightwave may be used for the irradiation. The present invention also offers a method of differentiation-inducing cells, in which the lightwave irradiation is performed for at most 10 minutes.

By implementing the above-described method, the differentiation induction can be performed even after the transplantation of the mesenchymal stem cells into a living body is completed. This broadens the range of medical care, which is advantageous.

According to the present invention, mesenchymal stem cells, which can differentiate to cells constituting various tissues and organs, can be selectively differentiation-induced to osteoblasts. Therefore, the regeneration of a bone tissue can be performed for a patient who needs bone transplantation.

BRIEF DESCRIPTION OF THE DRAWING

FIG. 10 is a graph showing the result of comparison between the amount of the mRNA of the cryptochrome in the cytoplasm of laser-irradiated cells and that of laser-unirradiated cells.

DETAILED DESCRIPTION OF THE INVENTION

Figures 1A, 1B:
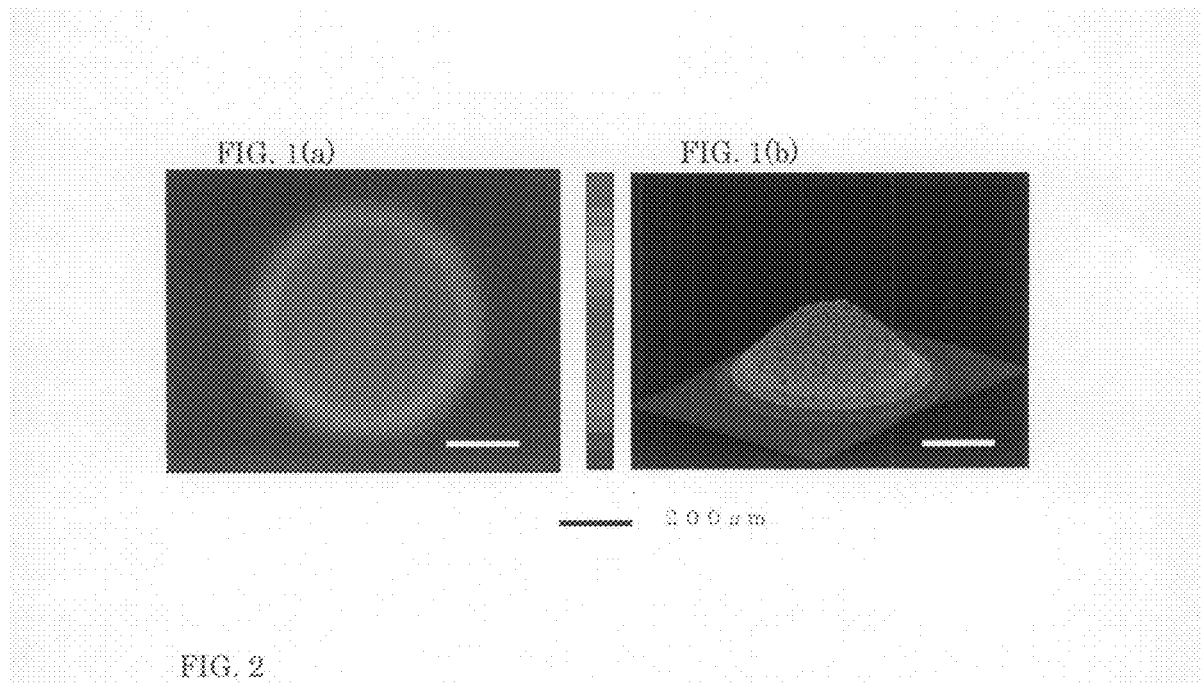
FIG. 1(a) shows the beam diameter of a laser lightwave emitted at a power density of 100 mW/cm$^2$ from a laser-lightwave irradiation device used in the present invention.
FIG. 1(b) shows the profile of the laser lightwave.

Next, the best mode for carrying out the present invention is explained below.

(a) Mesenchymal Stem Cells

In the present invention, mesenchymal stem cells separated from the bone marrow and fat tissue of an animal including the human can be utilized. In addition, already established mesenchymal stem cells can also be suitably used. For example, KUSA-A1 cells and KUSA-O cells are established mesenchymal stem cells derived from the bone marrow of a C3H/He mouse. They are registered at the RIKEN cell bank as RCB2081 and RCB1991. They are easily available cells when an application is made to the RIKEN cell bank.

KUSA-A1 cells and KUSA-O cells can be cultured in an ordinary DMEM medium containing 10% fetal bovine serum (FBS). In addition, they can be easily subcultured. When they are cultured in a medium to which a differentiation-inducing factor is added, such as ascorbate, dexamethasone, and β-glycerol phosphoric acid, KUSA-A1 cells and KUSA-O cells become a marker for the differentiation to osteoblasts. The accumulation of calcium can be confirmed by the increase in alkaline phosphatase activity and the staining with alizarin red S.

(b) Irradiation with a Lightwave Having a Specific Wavelength

As for the wavelength range of a lightwave having a specific wavelength to be used in the present invention, it is desirable that the lightwave have a wavelength range slightly shorter-wavelength-side in the visible light range, i.e., a wavelength range of 350 to 500 nm. A device that emits a lightwave having the above-described wavelength range can be suitably used. For example, the following lasers can be used: an argon laser that oscillates a laser lightwave having a wavelength of 488 nm, a GaN-based laser that oscillates a laser lightwave having a wavelength of 405 nm, and a helium-cadmium laser that oscillates a laser lightwave having a wavelength of 442 nm. When a device that oscillates a laser lightwave having the foregoing wavelength range and that can vary the power density is used, the amount of irradiation to the cells can be adjusted. Therefore, this type of device is more desirable.

The lightwave having a specific wavelength can be introduced either from the bottom face or the upper face of the culturing container. However, the mesenchymal stem cells are adherent cells that proliferate by adhering to the bottom face of the culturing container. Therefore, it is desirable to irradiate from the bottom face of the culturing container, because no interference is received from the culturing container, culture medium, and so on, so that the efficiency is increased.

It is desirable that the lightwave for the irradiation have a power density as large as possible because as the density increases, the activity of the differentiation induction to osteoblasts is increased, thereby advancing the accumulation of calcium. Nevertheless, as the power density is increased, the damage given to the cells is increased. In this case, therefore, the irradiation period must be shortened. This phenomenon has no tendency difference even when the wavelength of the employed lightwave is varied.

For example, in the case where a GaN-based laser that continuously oscillates a laser lightwave of 405 nm is used, when the irradiation is performed for at least 10 minutes at a power density of 300 mW/cm$^2$, about one-third of the cells suffer the stress. In the case of this laser, it is desirable that the irradiation be carried out for at most five minutes at a power density of at most 200 mW/cm$^2$, because the stress given to the cells is decreased.

(c) Cytotoxicity

Whether the cytotoxicity has occurred or not can be judged by using an existing method of measuring the activity of cytotoxicity. For example, first, mesenchymal stem cells are labeled with an radioactive isotope, such as $^{51}$Cr, or a fluorescent dye, such as europium. When the cell membrane is damaged by the lightwave irradiation, the measurement of the amount of $^{51}$Cr or europium leaking out of the inside of cells can be used for the judgement. In addition, the calculation with an MTT assay can also be used. In this case, first, an MTT, which is a tetrazolium salt, is added to the medium. If the cells are alive, the cells are reduced to a blue pigment (formazan) by the action of a dehydrogenase in the mitochondria. The MTT assay exploits this principle. Moreover, in recent years, the cytotoxicity activity can also be measured by measuring the amount of ATP in the cells with the luciferase emission analysis. In this method, the chemical luminescence by the luciferase is measured. Consequently, even when the number of cells is small, the measurement can be performed, which is advantageous.

In addition, the cytotoxicity can also be measured by the degree of accumulation of a heat shock protein (HSP70), which is a protein that appears when cells are subjected to stress. The accumulation degree of the HSP70 can be measured, for example, by the following method: First, a manifestation system is structured that is transfected with a luciferase gene at the downstream of the HSP70 gene promoter. Then, cells that are subjected to the gene transfection are used for the measurement. When the transfectant undergoes a stress such as a laser lightwave, the luciferase manifests itself by the action of the promoter of the HSP70. The measurement of the luciferase activity enables the measurement of the cytotoxicity activity. As the above-described cells, for example, the CHO (pMAM-HSluc) can be used suitably that is registered as JCRB0136.2 in the JCRB cell bank.

(d) Pretreatment of Cells

When a medium containing mesenchymal stem cells, such as KUSA-A1 cells or KUSA-O cells, is replaced with a medium containing dexamethasone, the manifestation of the gene of a biological clock-relevant factor is reset and newly induced (see Science, vol. 289, pp. 2344-2347, 2000). Consequently, in order to study the relationship between the manifestation of the biological clock-relevant factor and the differentiation induction to osteoblasts, it is desirable to culture mesenchymal stem cells in a dexamethasone-containing medium before the irradiation with a lightwave.

(e) Marker for the Cell Differentiation

The differentiation induction to osteoblasts can be confirmed with the measurement of alkaline phosphatase, alizarin red S staining, osteocalcin immunostaining, or von Kossa staining. The presence or absence of the differentiation induction to fat cells can be confirmed by the oil red O staining. The individual methods are explained below.

(e1) Measurement of Alkaline Phosphatase

The presence of alkaline phosphatase can be confirmed by a method of staining the cells or by the measuring of the enzyme reaction using a cell extract. The alkaline phosphatase is a protein produced at an early stage of the process in which mesenchymal stem cells are differentiated to osteoblasts. The confirmation of the production of this protein indicates the starting of the differentiation. The cell staining is a method in which, first, the differentiation-induced cells are fixed by using parafomaldehyde or the like and, then, the cells are stained by using, as the substrate of enzyme, a nitroblue tetrazolium salt (NBT), which is a substance insoluble in the water to be deposited to the cells afterward. The pigment to be used as the substrate is available in the market today in various types, and any type can be used suitably. On the other hand, in order to measure the enzyme reaction, first, various solutions are added to the cells to be homogenized. The homogenized cell extract is mixed with a water-soluble para-nitrophenylphosphate that is to become the substrate. When the alkaline phosphatase exists in the cell extract, the para-nitrophenylphosphate is dephosphorylated to become para-nitrophenol. When the absorption of the produced para-nitrophenol is measured, the amount of the alkaline phosphatase in the cells can be measured quantitatively.

(e2) Staining with the Alizarin Red S

The alizarin red S is a sodium salt in which the hydrogen neighboring to the hydroxyl group in an alizarin molecule is replaced with a sulfone group. This pigment has a property to combine with a metallic ion, so that it stains a calcium salt-deposited portion in a living body. Therefore, the pigment is suitable to examine the deposition of calcium, which is recognized when osteoblasts are formed.

(e3) Immunostaining of the Osteocalcin

The osteocalcin is a protein that is produced by differentiation-advanced osteoblasts. Consequently, it is a proper marker to confirm that the differentiation to osteoblasts is advancing without problem. After produced by osteoblasts, the osteocalcin is γ-carboxyglutamated (Gla) by a vitamin K-dependent carboxylase. The Gla-osteocalcin combines with the hydroxyapatite in a bone to be accumulated in the bone matrix. Thus, it contributes to the formation of the bone. Therefore, the measurement of the Gla-osteocalcin is useful because it becomes a marker for the bone formation. An antibody to the osteocalcin is available in the market in various types. When a monoclonal antibody specific to the Gla-osteocalcin is used, the degree of differentiation to osteoblasts can be confirmed.

(e4) Von Kossa Staining

The von Kossa staining is a staining method that detects the deposition of calcium phosphate among various types of calcium that are deposited to the matrix at the outside of the cells in the process of the differentiation to osteoblasts. The calcium component to be used for the bone formation is calcium phosphate (hydroxyapatite). The staining with the alizarin red S can detect the deposition of calcium. However, the von Kossa staining is suitable to judge whether or not the calcium is a calcium that contributes to the bone formation.

(e5) Oil Red O Staining

It is known that mesenchymal stem cells differentiate not only to osteoblasts but also to fat cells. Whether or not the differentiation to fat cells has advanced can be judged by conducting the oil red O staining. The oil red O staining is used as one of the methods to confirm the differentiation from fat precursor cells to fat cells. The oil red O is one type of azo dye. It is nonpolar and fat-soluble, so that when it is brought into contact with fat cells, it dissolves in a solvent of an intracellular lipid (triglyceride). Thus, the fat cells are dyed.

(f) Confirmation of the Translocation of a Biological Clock-Relevant Factor from the Inside of the Cytoplasm to the Inside of the Nucleus An explanation is given below to a method of confirming the translocation of a biological clock-relevant factor from the inside of the cytoplasm to the inside of the nucleus by using, as an example, cryptochrome, which is one of the biological clock-relevant factors. The confirmation of the localization of the cryptochrome can be performed by using the immunostaining. More specifically, an antibody specific to the cryptochrome is used as a primary antibody, and an antibody labeled with a fluorescent dye is used as a secondary antibody. Thus, the cryptochrome in the cells is fluoresceinated, enabling the examination of it with a fluorescent microscope. As the fluoresceinating dye, it is desirable to use a dye that emits fluorescence different from that emitted from the dye used for the cell nucleus in order to secure the contrast between the two. For example, when the cell nucleus is stained with diamidino-2-phenylindole (DAPI), this dye specifically combines with the DNA in the cell nucleus and emits blue fluorescence when irradiated with ultraviolet rays. Consequently, it is desirable to label the cryptochrome by using a dye that emits red fluorescence, such as rhodamine, texas red, phycoerythrin, or Cy3.

As described above, the translocation of the cryptochrome from the inside of the cytoplasm to the inside of the nucleus can be confirmed by a method of double staining the cells, in which method the cell nucleus is stained with DAPI and the cryptochrome is stained with a specific antibody. In the above, the explanation is given by using the cryptochrome as an example. Nevertheless, this method can be applied to other biological clock-relevant factors, such as a PERIOD, BMAL1, and CLOCK. In other words, the confirmation can be performed by using an antibody specific to an individual biological clock-relevant factor.

(g) RNA interference

The presence or absence of the manifestation of the biological clock-relevant factor can be confirmed by using RNA interference. More specifically, this technique combines an mRNA transcribed from a DNA that codes a biological clock-relevant factor, such as cryptochrome, with an siRNA.

Thus, this technique inhibits the translation to a protein. In other words, this technique performs the translation inhibition and produces a condition that there is no protein in the cells. Under this condition, the differentiation induction to osteoblasts can be examined, and the translocation of the cryptochrome from the inside of the cytoplasm to the inside of the nucleus can be confirmed. The sequence of the siRNA can be designed, first, by finding the first AA at 75-base or more downstream from the initiation codon of the mRNA that is intended to suppress from manifesting itself. Then, the sequence is determined to be the 19 consecutive bases following the AA. Whether or not the designed sequence of the siRNA is specific to the targeted gene can be confirmed by using, for example, BLAST-SEARCH of NCBI (www.ncbi.nlm.nih.gov/).

(h) Real-Time PCR

In addition, it is known that when the cryptochrome is translocated from the cytoplasm to the inside of the cell nucleus, a negative feedback is exercised to suppress the mRNA in the cytoplasm from manifesting itself. This phenomenon can be confirmed by comparing with the amount of the RNA in the cytoplasm. More specifically, a classic technique may be used that extracts the total RNA existing in the cytoplasm by the steps of a phenol/chloroform extraction, protease treatment, and alcohol sedimentation. In addition, the RNA in the cytoplasm may also be extracted by using a commercially available total RNA-refining kit, such as the RNAqueous (registered trademark) kit (made by Ambion). After the RNA in the cytoplasm is extracted, the DNA is disintegrated to prevent an error due to the inclusion of the DNA. Subsequently, the performing of a real-time PCR with the designed primer enables the measurement of the amount of the mRNA of the targeted substance in the cytoplasm.

The real-time PCR can be easily performed by using a commercially available reagent (for example, the SYBR ExScript RT-RCR kit, made by Takara Bio.) and a commercially available device (for example, the Smart Cycler, made by Takara bio.).

(i) Differentiation Induction of Mesenchymal Stem Cells with Laser-Lightwave irradiation.

In the above, an explanation is given to the items necessary to explain embodiments of the present invention. In order to actually differentiation-induce mesenchymal stem cells, it is recommended that the following steps be carried out.

First, mesenchymal stem cells, such as KUSA-A1 cells or KUSA-O cells, are cultured in a multiplate in the previous day. As for the multiplate, a 96-well multiplate is sufficiently used to examine the differentiation induction, depending on the size of the irradiation spot of the laser lightwave. The number of cells placed in the multiplate depends on the proliferation time and size of the cells to be tested. However, it is usually recommended that the cells be placed by a number of $1 \times 10^6$ sells/well or so. After an elapse of one day, the medium is replaced with a medium containing dexamethasone. It is desirable that the replacement be performed 30 to 60 minutes before the laser irradiation from the viewpoint of the transcription to the mRNA and the translation to the protein and so on.

Next, the laser lightwave is introduced from the bottom face of the 96-well multiplate. For example, the laser irradiation is performed at a power density of 200 mW/cm$^2$ for three minutes by using a GaN-based laser oscillation device that emits a laser lightwave of 405 nm. After the completion of the laser irradiation, the medium of the multiplate is replaced with a medium for the differentiation induction to osteoblasts to continue the culturing.

The cells are taken out after an elapse of five days of culturing in the medium for the differentiation induction to osteoblasts. The cells can be confirmed with the measurement of alkaline phosphatase, alizarin red S staining, osteocalcin immunostaining, or von Kossa staining. In addition, the presence or absence of the differentiation induction to fat cells can be confirmed by the oil red O staining.

The involvement of a specific biological clock-relevant factor, such as cryptochrome, can be examined by the following method. First, siRNA is further added to the medium for the differentiation induction to osteoblasts to perform the culturing. Then, a comparison is made with cells to which no siRNA is added.

EXAMPLES

An explanation is given below by referring to concrete examples. A method of differentiation-inducing cells of the present invention is not limited to the cells in the concrete examples. In addition, a device for irradiating a lightwave having a specific wavelength, also, is not limited to the one in the concrete examples. Furthermore, a technique for confirming the state of the differentiation to osteoblasts by taking out the cells to the outside of the living body is not limited to the method used in the examples.

Experimental Example 1

Differentiation Induction to Osteoblasts (a) Preparation of Cells

KUSA-A1 cells, which are one type of mesenchymal stem cells, were cultured in a DMEM medium containing 10% fetal bovine serum (FBS) by using a culturing flask of 75 cm$^2$. Cells at a logarithmic-growth phase were taken out the day before the day for the laser irradiation. The taking out was performed by the following way. First, the KUSA-A1 cells were floated from the bottom face of the culturing flask by using 0.25% trypsin. The number of cells was counted with a hemocytometer. A cell suspension was obtained by adjusting the number of cells to $1 \times 10^7$ cells/mL using a DMEM medium containing 10% FBS. The cell suspension was separately put into a 96-well multiplate (Falcon, made by Japan BD) at 100 µL/well. The cells were cultured one night at 37° C. and in an environment of 5% CO$_2$ using a CO$_2$ incubator.

(b) Laser Irradiation

The 96-well multiplate into which the KUSA-A1 cells were separately put in the previous day was taken out of the CO$_2$ incubator 30 minutes before the laser irradiation. A DMEM medium that contains 10% FBS containing 200-nM dexamethasone (Catalog No. 047-18863, made by Wako Pure Chemical Co.) was added to the wells at 100 µL/well to adjust the concentration of the dexamethasone to 100 nM. Thus, the manifestation of the biological clock-relevant gene was reset. Thirty minutes after, the laser irradiation was performed at varied power densities of 100, 200, and 300 mW/cm$^2$ for three minutes for an individual group of 24 wells by using a GaN-based laser irradiation device (VLM500, made by Sumitomo Electric Ind. Ltd.). As a control group, a group of 24 wells was not subjected to the laser-lightwave irradiation. FIG. 1(a) shows the beam diameter of a laser lightwave outputted at 100 mW/cm$^2$, and FIG. 1(b) shows the intensity distribution profile of the laser lightwave. It was confirmed that the laser lightwave had a beam diameter of 552 µm and a profile similar to a Gaussian distribution.

(c) Cell Culturing

After the completion of the laser-lightwave irradiation, the medium containing dexamethasone in each well was suction-removed with a capillary. Then, a medium for the differentiation induction to osteoblasts was separately put at 200 μL/well. In the above, the medium was prepared by adding 10-nM dexamethasone, 2-mM β-glycerol phosphoric acid, and 50-μg/mL ascorbic acid to a DMEM medium containing 10% FBS. Subsequently, the culturing was performed for five days at 37° C. and in an environment of 5% $CO_2$.

(d) Alizarin red S Staining

Figure 2:
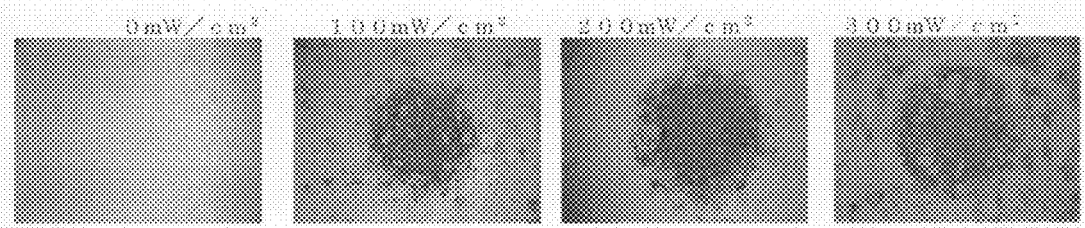
FIG. 2 shows the result of observation with a microscope to measure the deposition of calcium by using the alizarin red S staining after the differentiation induction to osteoblasts is performed for KUSA-A1 cells irradiated with a laser lightwave and KUSA-A1 cells unirradiated.

The alizarin red S staining was performed for the control group and three groups each consisting of three wells to which the laser-lightwave irradiation was performed at a power density of 100, 200, or 300 $mW/cm^2$ for each group. First, the media in the multiplate used for the five-day culturing were removed. After the wells were washed with PBS, 4% parafomaldehyde-PBS was added at 50 μL/well. By being placed under a stationary condition for five minutes, the cells were fixed. Next, an alizarin red staining liquid (made by Cosmo Bio) was added at 50 μL/well. Moreover, after leaving them stationary for five minutes, PBS washing was performed. Then, the observation was made using an inverted microscope at 50 power to measure the deposition of the alizarin red S. The observation results are shown in FIG. 2. The circular black portion in FIG. 2 is the laser lightwave-irradiated portion. The calcium produced from the KUSA-A1 cells in the irradiated spot is stained by the alizarin red S in reddish brown (black in FIG. 2). The stained intensity at the irradiation of 200 and 300 $mW/cm^2$ is greater than that at the irradiation of 100 $mW/cm^2$.

(e) Von Kossa Staining

Figure 3:
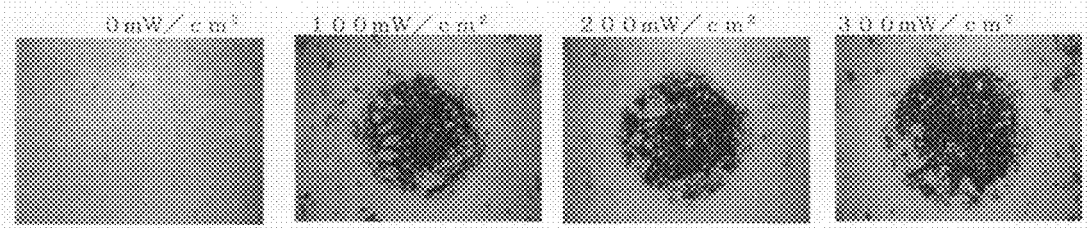
FIG. 3 shows the result of observation with a microscope to measure the deposition of calcium phosphate by using the von Kossa staining after the differentiation induction to osteoblasts is performed for KUSA-A1 cells irradiated with a laser lightwave and KUSA-A1 cells unirradiated.

The von Kossa staining was performed for the control group and three groups each consisting of three wells to which the laser-lightwave irradiation was performed at a power density of 100, 200, or 300 $mW/cm^2$ for each group. First, the media in the multiplate used for the five-day culturing were removed. After the wells were washed with PBS, 4% parafomaldehyde-PBS was added at 50 μL/well. By being placed under a stationary condition for five minutes, the cells were fixed. Next, a staining liquid (made by Sigma) was added at 50 μL/well. Moreover, after leaving them stationary for five minutes, distilled water washing was performed. Subsequently, a photograph-use developing solution (a 5% sodium thiosulfate aqueous solution) was used to produce deep-blackish brown metallic silver, which is reductive chromogenic. Then, the observation was made using an inverted microscope at 50 power to measure the deposition of calcium phosphate (hydroxyapatite). The observation results are shown in FIG. 3. The circular black portion in FIG. 3 is the laser lightwave-irradiated portion. The calcium phosphate produced from the KUSA-A1 cells in the irradiated spot is stained by the above-described metallic silver (black in FIG. 3). The stained intensity at the irradiation of 200 and 300 $mW/cm^2$ is greater than that at the irradiation of 100 $mW/cm^2$.

(f) Alkaline Phosphatase Staining

Figure 4:
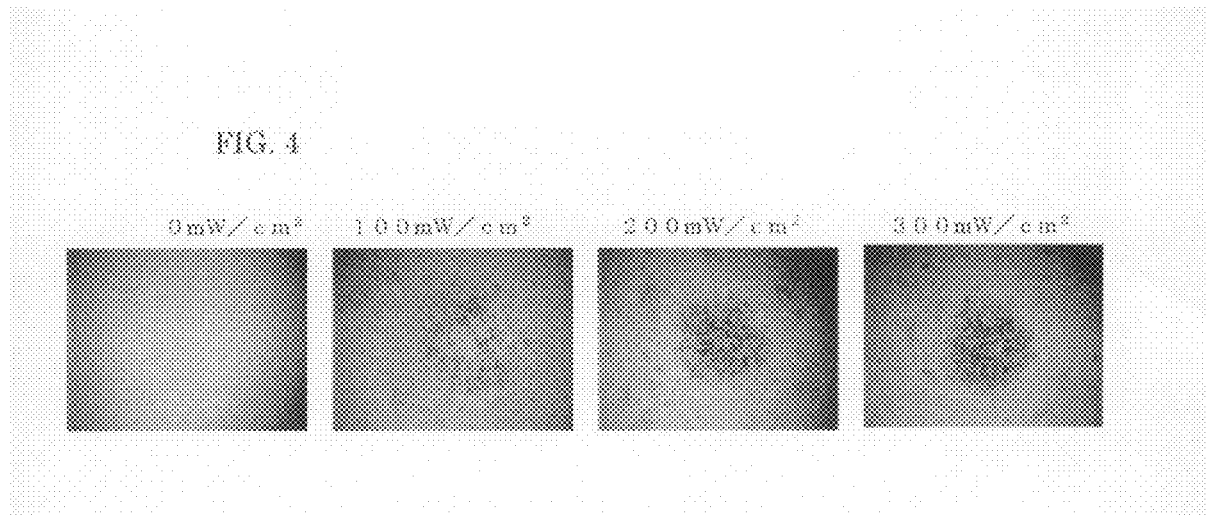
FIG. 4 shows the result of observation with a microscope to measure the alkaline phosphatase activity after the differentiation induction to osteoblasts is performed for KUSA-A1 cells irradiated with a laser lightwave and KUSA-A1 cells unirradiated.

The alkaline phosphatase staining was performed for the control group and three groups each consisting of three wells to which the laser-lightwave irradiation was performed at a power density of 100, 200, or 300 $mW/cm^2$ for each group. First, the media in the multiplate used for the five-day culturing were removed. After the wells were washed with PBS, 4% parafomaldehyde-PBS was added at 50 μL/well. By being placed under a stationary condition for five minutes, the cells were fixed. Next, the Vector (R)-Black Alkaline Phosphatase Substrate Kit II (manufacturing No. SK-5200, made by Funakoshi) was added at 50 μL/well. Moreover, after leaving them stationary for five minutes, PBS washing was performed. Then, the observation was made using an inverted microscope at 50 power to measure the deposition of the black pigment produced by the action of the alkaline phosphatase. The observation results are shown in FIG. 4. The circular black portion in FIG. 4 is the laser lightwave-irradiated portion. A reddish black pigment was deposited on the KUSA-A1 cells in the irradiated spot. The stained intensity at the irradiation of 200 and 300 $mW/cm^2$ is greater than that at the irradiation of 100 $mW/cm^2$.

(g) Osteocalcin Immunostaining

Figure 5:
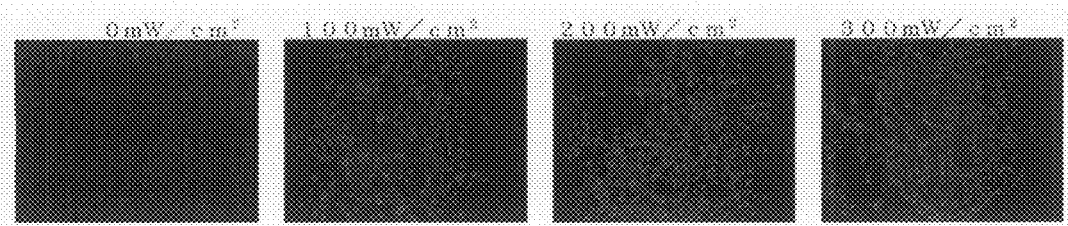
FIG. 5 shows the result of observation with a microscope to measure the manifestation of the osteocalcin after the differentiation induction to osteoblasts is performed for KUSA-A1 cells irradiated with a laser lightwave and KUSA-A1 cells unirradiated.

The osteocalcin immunostaining was performed for the control group and three groups each consisting of three wells to which the laser-lightwave irradiation was performed at a power density of 100, 200, or 300 $mW/cm^2$ for each group. First, the media in the multiplate used for the five-day culturing were removed. After the wells were washed with PBS, 4% parafomaldehyde-PBS was added at 50 μL/well. By being placed under a stationary condition for five minutes, the cells were fixed. Next, a block ace solution (made by Dainippon Pharmaceutical Co. Ltd.) diluted with distilled water at a 4-fold dilution factor was separately put at 100 μL/well to perform the blocking for one hour at room temperature. The fixed cells were washed three times with PBS containing 0.1% Tween 20. An antibody specific to Gla-osteocalcin was separately put at 50 μL/well to make them perform a reaction for one hour at room temperature. In the above description, the antibody used was a rabbit-derived anti-mouse osteocalcin (LB-4005, made by LSL Co.). The fixed cells were washed three times with PBS containing 0.1% Tween 20. A Cy3-labeled anti-rabbit antibody (made by Sigma) was separately put at 50 μL/well to further make them perform a reaction for one hour at room temperature. The fixed cells were washed three times with PBS containing 0.1% Tween 20. Then, the observation was made using a fluorescent inverted microscope at 50 power to examine the result of the fluorescent staining with the osteocalcin. The observation results are shown in FIG. 5. The circular red portion in FIG. 5 is the laser lightwave-irradiated portion. It was recognized that the KUSA-A1 cells at the irradiated spot manifested the osteocalcin and were stained in red. The stained intensity at the irradiation of 200 and 300 $mW/cm^2$ is greater than that at the irradiation of 100 $mW/cm^2$.

(h) Oil Red O Staining

Figure 6:
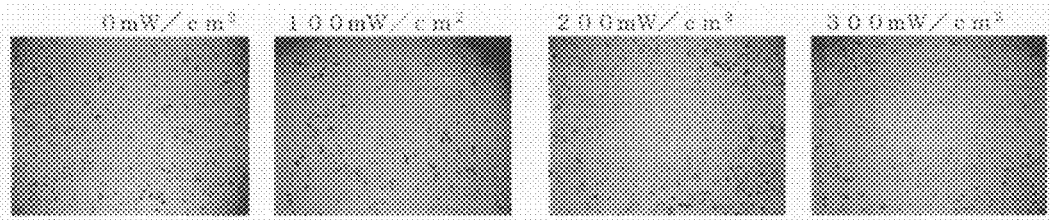
FIG. 6 shows the result of observation with a microscope to measure, by using the oil red O staining, the number of cells that have differentiated to fat cells after the differentiation induction to osteoblasts is performed for KUSA-A1 cells irradiated with a laser lightwave and KUSA-A1 cells unirradiated.

The oil red O staining was performed for the control group and three groups each consisting of three wells to which the laser-lightwave irradiation was performed at a power density of 100, 200, or 300 $mW/cm^2$ for each group. First, the media in the multiplate used for the five-day culturing were removed. After the wells were washed with PBS, 4% parafomaldehyde-PBS was added at 50 μL/well. By being placed under a stationary condition for five minutes, the cells were fixed. Next, an oil red O staining liquid was separately put at 50 μL/well to perform the staining. In the above description, the oil red O staining liquid was a liquid in which 0.5 gram of oil red O was dissolved in 100 mL of isopropyl alcohol. After the staining for 30 minutes, PBS washing was performed. Then, the observation was made using an inverted microscope at 50 power to measure the deposition of the oil red O pigment. The observation results are shown in FIG. 6. In FIG. 6, also, the circular portion similar to that shown in FIGS. 2 to 5 was irradiated with a laser lightwave. However, the deposition of the oil red O was not recognized in the KUSA-A1 cells both in the irradiated wells and in the unirradiated wells. This result shows that a violet laser lightwave does not turn on the switch for the differentiation induction to fat cells.

Experimental Example 2

Measurement of Cytotoxic Activity (a) Laser-Lightwave Irradiation to Cells

The cytotoxic activity was measured by the following way. First, CHO (pMAM-HSluc) cells were cultured in a culturing flask of 75 $cm^2$. The cultured cells were floated by a 0.25% trypsin treatment. A cell suspension was pre-pared by adjusting the number of cells to $1\times10^7$ cells/mL by using a DMEM medium containing 10% FBS. The cell suspension was separately put into a 96-well multiplate (Falcon, made by Japan BD) at 100 µL/well. The cells were cultured one night at 37° C. and in an environment of 5% $CO_2$. Subsequently, a laser-lightwave irradiation was performed at varied power densities of 50, 100, 200, 300, and 400 mW/$cm^2$ by using a GaN-based laser irradiation device (VLM500, made by Sumitomo Electric Ind. Ltd.). The irradiation period was also varied to 1, 3, 5, and 10 minutes. The irradiation was performed to the individual groups of three wells by varying the irradiating condition as described above. As a control group, a group of three wells was also prepared to which no laser-lightwave irradiation was performed. After the irradiation, the cells were cultured one night at 37° C. and in an environment of 5% $CO_2$.

(b) Measurement of Cytotoxic Activity

Figure 7:
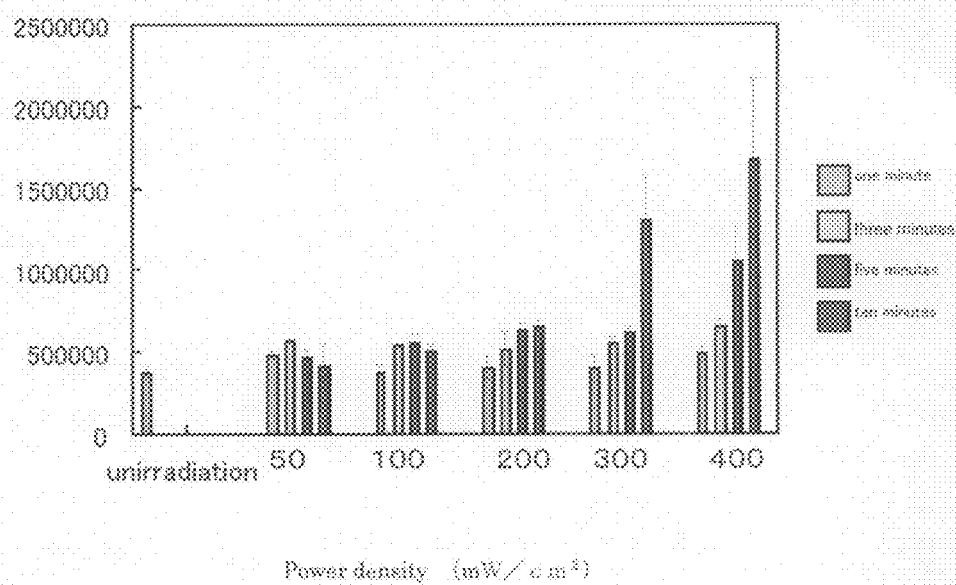
FIG. 7 shows the result of measurements of the amount of luciferase after CHO (pMAM-HSluc) cells are irradiated with a laser lightwave by varying the power density.

In the next day, a luciferase activity was measured by using a luciferase-measuring system (a homogenous, high-sensitivity type) (made by Promega). The result is shown in FIG. 7. As shown in FIG. 7, when the laser-lightwave irradiation is performed at a power density of 50, 100, or 200 mW/$cm^2$, the intensity of the chemiluminescence is 500,000 RTU or less. In other words, the luciferase activity is comparable to that of the control group, the manifestation of HSP70 is small, the cells are free from stress, and no damage in the cells is recognized. On the other hand, when the laser-lightwave irradiation is performed at a power density of 300 mW/$cm^2$ for 10 minutes or at a power density of 400 mW/$cm^2$ for 5 minutes or more, the intensity becomes 1,500,000 RTU or so. In other words, an intense manifestation of HSP70 is recognized, the cells are subjected to high stress, and damage in the cells is recognized.

Experimental Example 3

Suppression of the Manifestation of Cryptochrome (a) Design of siRNA

To examine whether or not cryptochrome is a molecule whose switch is turned on by a violet laser lightwave, a test was performed using the siRNA of cryptochrome. For the sequence of the siRNA, two types of siRNA were designed that have sense strands of the SEQ ID NO: 1, which is 5'-GCAGACUGAAUAUUGAAAGTT-3', and the SEQ ID NO: 2, which is 5'-GGCACUUACACGUUUGGAATT-3'. In the above, the sequence is designed based on the sequence of the mRNA of the cryptochrome. The production of the sense strand and antisense strand of each of the SEQ ID NOS: 1 and 2 and their annealing were outsourced to Ambion Inc.

(b) Transfection of the siRNA

The preparation of cells and transfection to them were performed by the following way. First, KUSA-A1 cells were cultured in a culturing flask of 75 $cm^2$. The cultured cells were floated by a 0.25% trypsin treatment. A cell suspension was prepared by adjusting the number of cells to $1\times10^5$ cells/mL by using a DMEM medium containing 10% FBS. The cell suspension was separately put into a 96-well multiplate (Falcon, made by Japan BD) at 100 µL/well. The cells were cultured one night at 37° C. and in an environment of 5% $CO_2$. In the next day, the medium was suction-removed. The well was washed once with a DME medium. A DME medium was added at 100 µL/well. Then, pre-treated siRNA was adjusted to 20 µM. The siRNA solution was diluted at a 100-fold dilution factor in an DMEM medium to prepare a volume of 90 µL. Separately, 3 µL of oligofectamine (made by Invitrogen Co.) for the transfection was diluted to 10 µL with a DME medium. After placed under a stationary condition for 10 minutes at room temperature, the diluted oligofectamine was slightly mixed with the siRNA solution. The mixture was further placed under a stationary condition for 20 minutes at room temperature. Thus, an siRNA transfection solution was prepared. Twenty minutes after, the siRNA transfection solution was separately put into the individual wells at 1 µL/well. The solution was placed under a stationary condition for four hours at 37° C. and in an environment of 5% $CO_2$. Subsequently, FBS was added at 10 µL/well to complete the transfection to the cells.

(c) Laser-Lightwave Irradiation to the siRNA Transfectant

The multiplate into which the transfection-treated cells were placed was taken out from the $CO_2$ incubator having an inside environment of 5% $CO_2$ at 37° C. Then, 30 minutes before the laser irradiation, a DMEM medium that contains 10% FBS containing 200-nM dexamethasone (Catalog No. 047-18863, made by Wako Pure Chemical Co.) was added to the wells at 100 µL/well to adjust the concentration of the dexamethasone to 100 nM. Thus, the manifestation of the biological clock-relevant gene was reset. Thirty minutes after, the laser irradiation was performed at varied power densities of 100, 200, and 300 mW/$cm^2$ for three minutes by using a GaN-based laser irradiation device (VLM500, made by Sumitomo Electric Ind. Ltd.).

(d) Cell Culturing

After the laser-lightwave irradiation, the cells were cultured with a method similar to that used in Experimental example 1. More specifically, after the completion of the laser-lightwave irradiation, the medium containing dexamethasone in each well was suction-removed with a capillary. Then, a medium for the differentiation induction to osteoblasts was separately put at 200 µL/well. In the above, the medium was prepared by adding 10-nM dexamethasone, 2-mM β-glycerol phosphoric acid, and 50-µg/mL ascorbic acid to a DMEM medium containing 10% FBS. Subsequently, the culturing was performed for five days at 37° C. and in an environment of 5% $CO_2$.

(e) Alizarin Red S Staining

Figure 8:
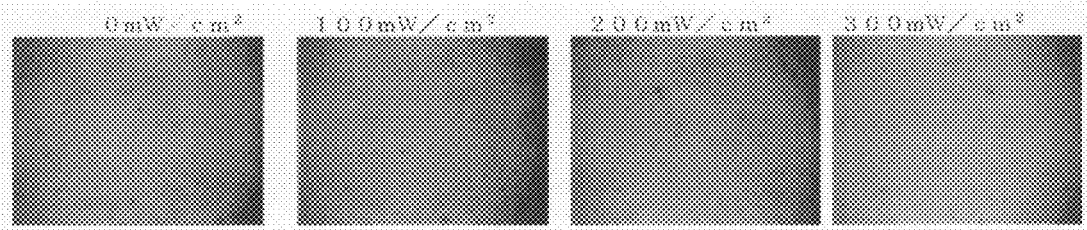
FIG. 8 shows the result of observation with a microscope to measure the deposition of calcium by using the alizarin red S staining after the differentiation induction to osteoblasts is performed by adding siRNA to the cryptochrome in KUSA-A1 cells irradiated with a laser lightwave and KUSA-A1 cells unirradiated.

The alizarin red S staining was performed for the control group and three groups each consisting of three wells to which the laser-lightwave irradiation was performed at a power density of 100, 200, or 300 mW/$cm^2$ for each group. First, the media in the multiplate used for the five-day culturing were removed. After the wells were washed with PBS, 4% parafomaldehyde-PBS was added at 50 µL/well. By being placed under a stationary condition for five minutes, the cells were fixed. Next, an alizarin red staining liquid (made by Cosmo Bio) was added at 50 μL/well. Moreover, after leaving them stationary for five minutes, PBS washing was performed. Then, the observation was made using an inverted microscope at 50 power to measure the deposition of the alizarin red S. The observation results are shown in FIG. 8. As can be seen from FIG. 8, when siRNA, which suppresses the manifestation of cryptochrome, is added, even the KUSA-A1 cells in the laser lightwave-irradiated circular portion is not stained by the alizarin red S.

Experimental Example 4

Property of Cryptochrome to Localize in a Cell (a) Preparation of Cells

KUSA-A1 cells, which are one type of mesenchymal stem cells, were cultured in a DMEM medium containing 10% fetal bovine serum (FBS) by using a culturing flask of 75 $cm^2$. Cells at a logarithmic-growth phase were taken out the day before the day for the laser irradiation. The taking out was performed by the following way. First, the KUSA-A1 cells were floated from the bottom face of the culturing flask by using 0.25% trypsin. The number of cells was counted with a hemocytometer. A cell suspension was obtained by adjusting the number of cells to $1\times10^7$ cells/mL using a DMEM medium containing 10% FBS. The cell suspension was separately put into a 96-well multiplate (Falcon, made by Japan BD) at 100 μL/well. The cells were cultured one night at 37° C. and in an environment of 5% $CO_2$ using a $CO_2$ incubator.

(b) Laser Irradiation

The 96-well multiplate into which the KUSA-A1 cells were separately put in the previous day was taken out from the $CO_2$ incubator 30 minutes before the laser irradiation. A DMEM medium that contains 10% FBS containing 200-nM dexamethasone (Catalog No. 047-18863, made by Wako Pure Chemical Co.) was added to the wells at 100 μL/well to adjust the concentration of the dexamethasone to 100 nM. Thus, the manifestation of the biological clock-relevant gene was reset. Thirty minutes after, the laser irradiation was performed at varied power densities of 100, 200, and 300 mW/$cm^2$ for three minutes for an individual group of three wells by using a GaN-based laser irradiation device (VLM500, made by Sumitomo Electric Ind. Ltd.).

(c) Cell Culturing

After the completion of the laser-lightwave irradiation, the medium containing dexamethasone in each well was suction-removed with a capillary. Then, a medium for the differentiation induction to osteoblasts was separately put at 200 μL/well. In the above, the medium was prepared by adding 10-nM dexamethasone, 2-mM β-glycerol phosphoric acid, and 50-μg/mL ascorbic acid to a DMEM medium containing 10% FBS. Subsequently, the culturing was performed for five days at 37° C. and in an environment of 5% $CO_2$.

(d) The Cryptochrome Immunostaining and Cell Nucleus Staining of Cells Differentiation-Induced to Osteoblasts First, the media in the multiplate used for the five-day culturing were removed. After the wells were washed with PBS, 4% parafomaldehyde-PBS was added at 50 μL/well. By being placed under a stationary condition for five minutes, the cells were fixed. Next, a block ace solution (made by Dainippon Pharmaceutical Co. Ltd.) diluted with distilled water at a 4-fold dilution factor was separately put at 100 μL/well to perform the blocking for one hour at room temperature. The fixed cells were washed three times with PBS containing 0.1% Tween 20. An antibody specific to cryptochrome was separately put at 50 μL/well to make them perform a reaction for one hour at room temperature. In the above description, the antibody used was a rabbit-derived anti-mouse cryptochromel (cryll-A, made by Alpha Diagnostic Co.). The fixed cells were washed three times with PBS containing 0.1% Tween 20. A Cy3-labeled anti-rabbit antibody (made by Funakoshi) was separately put at 50 μL/well to further make them perform a reaction for one hour at room temperature. The fixed cells were washed three times with PBS containing 0.1% Tween 20. Then, the cryptochrome was fluorescent stained. The cell nucleus was stained with DAPI. In the above, the DAPI was adjusted with methanol to 2 mg/mL to prepare a liquid. The liquid was diluted with PBS at a 1,000-fold dilution factor. A proper amount of the diluted liquid was placed on the cells to place under a stationary condition for five minutes.

Figure 9:
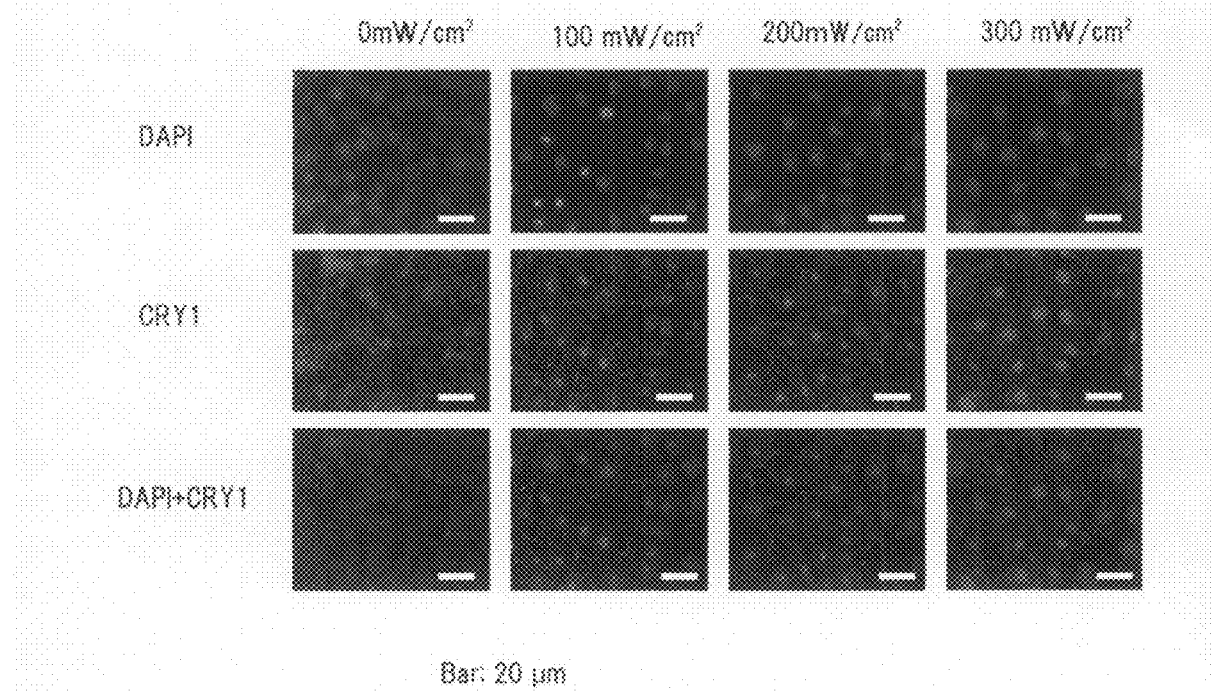
FIG. 9 shows the result of observation with a microscope to measure the property of cryptochrome to localize in a cell by using a double-staining method composed of immunostaining and nucleus staining after the differentiation induction to osteoblasts is performed for KUSA-A1 cells irradiated with a laser lightwave and KUSA-A1 cells unirradiated.

The double-stained cells were observed with a fluorescent inverted microscope at 200 power. The observed results are shown in FIG. 9. In the cells unirradiated with a laser lightwave, the blue nucleus stained by DAPI does not overlap with the red portion that shows the manifestation of the cryptochrome. This result shows that the cryptochrome localizes in the cytoplasm. On the other hand, in the cells irradiated with a laser lightwave at a power density of 100, 200, or 300 mW/$cm^2$, the blue nucleus stained by DAPI overlaps with the red portion that shows the manifestation of the cryptochrome. This result confirms that the cryptochrome has been translocated to the nucleus.

Experimental Example 5

Negative Feedback Control of Cryptochrome (a) Preparation of Cells

KUSA-A1 cells, which are one type of mesenchymal stem cells, were cultured in a DMEM medium containing 10% fetal bovine serum (FBS) by using a culturing flask of 75 $cm^2$. Cells at a logarithmic-growth phase were taken out the day before the day for the laser irradiation. The taking out was performed by the following way. First, the KUSA-A1 cells were floated from the bottom face of the culturing flask by using 0.25% trypsin. The number of cells was counted with a hemocytometer. A cell suspension was obtained by adjusting the number of cells to $1\times10^7$ cells/mL using a DMEM medium containing 10% FBS. The cell suspension was separately put into a 96-well multiplate (Falcon, made by Japan BD) at 100 μL/well. The cells were cultured one night at 37° C. and in an environment of 5% $CO_2$ using a $CO_2$ incubator.

(b) Laser Irradiation

The 96-well multiplate into which the KUSA-A1 cells were separately put in the previous day was taken out from the $CO_2$ incubator 30 minutes before the laser irradiation. A DMEM medium that contains 10% FBS containing 200-nM dexamethasone (Catalog No. 047-18863, made by Wako Pure Chemical Co.) was added to the wells at 100 μL/well to adjust the concentration of the dexamethasone to 100 nM. Thus, the manifestation of the biological clock-relevant gene was reset. Thirty minutes after, the laser irradiation was performed at a power density of 100 mW/$cm^2$ for three minutes by using a GaN-based laser irradiation device (VLM500, made by Sumitomo Electric Ind. Ltd.).

(c) Cell Culturing

After the completion of the laser-lightwave irradiation, the medium containing dexamethasone in each well was suction-removed with a capillary. Then, a medium for the differentiation induction to osteoblasts was separately put at 200 μL/well. In the above, the medium was prepared by adding 10-nM dexamethasone, 2-mM β-glycerol phosphoric acid, and 50-μg/mL ascorbic acid to a DMEM medium containing 10% FBS. Subsequently, the culturing was performed for 24 hours at 37° C. and in an environment of 5% $CO_2$.

(d) Extraction of Total RNA

The cells cultured for 24 hours after the completion of the laser irradiation were taken out. The total RNA was extracted from the cells by using the RNAqueous (registered trademark) kit (Catalog No, AM1912, made by Ambion) and by following the appended instruction manual. In addition, as a comparison sample, the total RNA was also extracted similarly from cells unirradiated with a laser lightwave. To remove the DNA included in the extracted specimen, both the total RNA extracted from the laser lightwave-irradiated cells and the total RNA extracted from the laser lightwave-unirradiated cells were treated with a DNA-degrading enzyme (DNase I, Catalog No. 2215A, made by Takara Bio.).

(e) Real-Time PCR

The real-time PCR was performed by using the Smart Cycler II (SC200N, made by Takara Bio.) as a real-time PCR device and by using the SYBR ExScript RT-RCR kit (Catalog No. RR053A, made by Takara Bio.) as a PCR kit. The PCR was performed by pouring into an exclusive-use tube the foregoing SYBR ExScript RT-RCR kit and the siRNA of the cryptochrome of sequence No. 1. Before starting the PCR, they were maintained at 95° C. for 15 minutes to activate Taq DNA polymerase. The following heat cycle of the PCR was repeated 40 times: (a) at 94° C. for 15 seconds, to (b) at 56° C. for 30 seconds, and to (c) at 72° C. for 30 seconds. The amount of the product by the PCR was measured by measuring the amount of the fluorescent pigment after the elongation reaction at each cycle. To exactly compare the amount of the mRNA of the cryptochrome in the laser-irradiated cells with that in the laser-unirradiated cells, a correction was made by measuring the amount of the mRNA of the 18S ribosomal protein in the total RNA of each group of the laser-irradiated cells and the laser-unirradiated cells. After the above-described correction, the amounts of the mRNA of the cryptochrome in the laser-irradiated cells and the laser-unirradiated cells were subjected to a significant-difference test at a significant level of 1% using the Student's t-test. The result is shown in FIG. 10. As shown in FIG. 10, the amount of the mRNA of the cryptochrome in the cytoplasm of the laser-irradiated cells is statistically significantly smaller than that of the laser-unirradiated cells. This result confirms that a negative feedback control is exercised by the translocation of the cryptochrome from the cytoplasm to the cell nucleus.

When a method of differentiation-inducing cells of the present invention is used, mesenchymal stem cells can be selectively differentiation-induced to osteoblasts. Consequently, the regeneration of a bone tissue can be effectively performed for a patient who needs bone transplantation. What is more, the switch for the differentiation induction to osteoblasts can be turned on by the irradiation with a lightwave having a specific wavelength that is noninvasive to the patient. Therefore, even after mesenchymal stem cells are transplanted to a patient, the differentiation induction can be performed, so that the burden on the patient can be reduced. This technique will lead to the development of a medical device for irradiating an affected portion with a lightwave with high efficiency. As a result, the growth of a medical-device industry can be expected.

What is claimed is:

1. An in vitro method of inducing mesenchymal stem cells to differentiate into osteoblasts by translocating biological clock-relevant factors of the mesenchymal stem cells from the cells' cytoplasm to the cells' nucleus, the method comprising irradiating the mesenchymal stem cells with a light having a wavelength of 350 to 500 nm, and after irradiation, culturing the cells in a medium comprising β-glycerol phosphoric acid.

2. The method according to claim 1 wherein the irradiation is performed by using a laser lightwave.

3. The method according to claim 1 wherein the irradiation is performed for at most 10 minutes.

4. The method according to claim 2 wherein the irradiation is performed for at most 10 minutes.

5. The method according to claim 1 wherein the biological clock-relevant factors are cryptochrome.

6. The method according to claim 2, wherein the biological clock-relevant factors are cryptochrome.

7. The method according to claim 3 wherein the biological clock-relevant factors are cryptochrome.

8. The method according to claim 4 wherein the biological clock-relevant factors are cryptochrome.

* * * * *